United States Patent
Qian et al.

(10) Patent No.: US 9,370,305 B2
(45) Date of Patent: Jun. 21, 2016

(54) METHOD AND SYSTEM FOR INTELLIGENT LINKING OF MEDICAL DATA

(75) Inventors: Yuechen Qian, Briarcliff Manor, NY (US); Merlijn Sevenster, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 205 days.

(21) Appl. No.: 14/005,399

(22) PCT Filed: Feb. 13, 2012

(86) PCT No.: PCT/IB2012/050635
§ 371 (c)(1),
(2), (4) Date: Sep. 16, 2013

(87) PCT Pub. No.: WO2012/123829
PCT Pub. Date: Sep. 20, 2012

(65) Prior Publication Data
US 2014/0003697 A1 Jan. 2, 2014

Related U.S. Application Data

(60) Provisional application No. 61/453,155, filed on Mar. 16, 2011.

(51) Int. Cl.
*G06K 9/00* (2006.01)
*A61B 5/00* (2006.01)
(Continued)

(52) U.S. Cl.
CPC ............ *A61B 5/0033* (2013.01); *G06F 19/321* (2013.01); *G06K 9/6201* (2013.01);
(Continued)

(58) Field of Classification Search
CPC ................... G06F 17/30247; G06F 17/30259;
G06F 17/3069; G06F 2212/454; G06K 9/42;
G06K 9/6211; G06K 9/627; G06T 2207/1008;
G06T 2207/30004; G06T 2207/30068
See application file for complete search history.

(56) References Cited

U.S. PATENT DOCUMENTS 6,320,976 B1 * 11/2001 Murthy et al. ................ 382/128
7,616,799 B2 11/2009 Ramamurthy et al.
(Continued)

FOREIGN PATENT DOCUMENTS

WO 0025255 A1 5/2000
WO 2007059615 A1 5/2007

OTHER PUBLICATIONS

Abou-Moustafa et al., Relaxed Exponential Kernels for Unsupervised Learning, 2011, R. Mester and M. Felsberg (Eds.): DAGM 2011, LNCS 6835, pp. 184-195.*
(Continued)

*Primary Examiner* — Vu Le
*Assistant Examiner* — Guillermo Rivera-Martinez

(57) ABSTRACT

Described herein are systems and methods for intelligently combining medical findings received across different modalities. The system comprises an extraction module extracting contextual information from an image of an area of interest including annotations, a feature selection module building a current feature vector using the extracted contextual information and the annotations, and a referencing engine computing a similarity score between the current feature vector and a prior feature vector of a prior image. The method comprises extracting contextual information from an image of an area of interest including annotations, building a current feature vector using the extracted contextual information and the annotations, and computing a similarity score between the current feature vector and a prior feature vector of a prior image.

20 Claims, 4 Drawing Sheets

(51) Int. Cl.
*G06F 19/00* (2011.01)
*G06K 9/62* (2006.01)
*G06T 7/00* (2006.01)

(52) U.S. Cl.
CPC ..... *G06T7/0014* (2013.01); *G06T 2207/10088* (2013.01); *G06T 2207/10116* (2013.01); *G06T 2207/10136* (2013.01); *G06T 2207/30068* (2013.01)

(56) References Cited

U.S. PATENT DOCUMENTS

| 7,814,040 | B1 | 10/2010 | Zhang et al. | |
| 2006/0027928 | A1 | 2/2006 | Funakoshi et al. | |
| 2009/0116765 | A1* | 5/2009 | Bystrov et al. | 382/294 |
| 2010/0099974 | A1 | 4/2010 | Desai | |
| 2011/0122138 | A1* | 5/2011 | Schmidt et al. | 345/440 |
| 2012/0233188 | A1* | 9/2012 | Majumdar | 707/756 |

OTHER PUBLICATIONS

Tahmoush, D et al. "A web collaboration system for content-based image retrieval of medical images," Proceedings of SPIE Medical Imaging 2007—PACS and Imaging Informatics, vol. 6516 p. 11PP, San Diego, CA., Feb. 2007.

Tahmoush, D. "A learned distance function for medical image similarity retrieval", Proc. SPIE 7264, Medical Imaging 2009: Advanced PACS-based Imaging Informatics and Therapeutic Applications, 726406 (Mar. 13, 2009); doi:10.1117/12.811365; http://dx.doi.org/10.1117/12.811365.

Elter, M. et al. "CADx of mammographic masses and clustered microcalcifications: A review". Medical Physics. vol. 36, No. 6, May 5, 2009, pp. 2052-2068.

* cited by examiner

METHOD AND SYSTEM FOR INTELLIGENT LINKING OF MEDICAL DATA

This application is a national stage application under 35 U.S.C. §371 of International Application No. PCT/IB2012/050635 filed on Feb. 13, 2012 and published in the English language on Sep. 20, 2012, as International Publication No. WO/2012/123829, which claims priority to U.S. Application No. 61/453,155 filed on Mar. 16, 2011, the entire disclosures of which are incorporated herein by reference.

BACKGROUND

Physicians such as radiologists and oncologists are dealing with increasing amounts of information to diagnose in order to treat patients optimally. For instance, patients with cancer frequently undergo imaging exams, and over time, will have dozens of studies in their medical record. Each time physicians read a new exam, they need to compare the current exam with prior ones in order to determine the progress of previously identified lesions and/or to discover any new lesions. This task requires the physicians to read, compare, interpret and correlate findings in both images and reports. These activities are both time-consuming from a workflow perspective and challenging from a clinical perspective.

Within the field of breast cancer treatment, mammography is the process of using low-dose amplitude X-rays (i.e., around 0.7 mSv) to examine the human breast in coordination with diagnostic and screening tools. The goal of mammography is the early detection of breast cancer, typically through detection of characteristic masses, lesions, and/or microcalcifications. Mammography is believed to reduce mortality from breast cancer. No other imaging technique has been shown to reduce risk, but remaining aware of breast changes and physician examination are considered essential parts of regular breast care. Accordingly, accurately and consistently annotating lesions is very important for clinical decision support.

SUMMARY OF THE INVENTION

Described herein is a system comprising an extraction module extracting contextual information from an image of an area of interest including annotations, a feature selection module building a current feature vector using the extracted contextual information and the annotations, and a referencing engine computing a similarity score between the current feature vector and a prior feature vector of a prior image.

Further described herein is a method comprising extracting, by an extraction module, contextual information from an image of an area of interest including annotations, building, a feature selection module, a current feature vector using the extracted contextual information and the annotations, and computing, by a referencing engine, a similarity score between the current feature vector and a prior feature vector of a prior image.

Further described herein is a non-transitory computer readable storage medium including a set of instructions that are executable by a processor, the set of instructions being operable at least to extract contextual information from an image of an area of interest including annotations, build a current feature vector using the extracted contextual information and the annotations, and compute a similarity score between the current feature vector and a prior feature vector of a prior image

DETAILED DESCRIPTION

Figure 1:
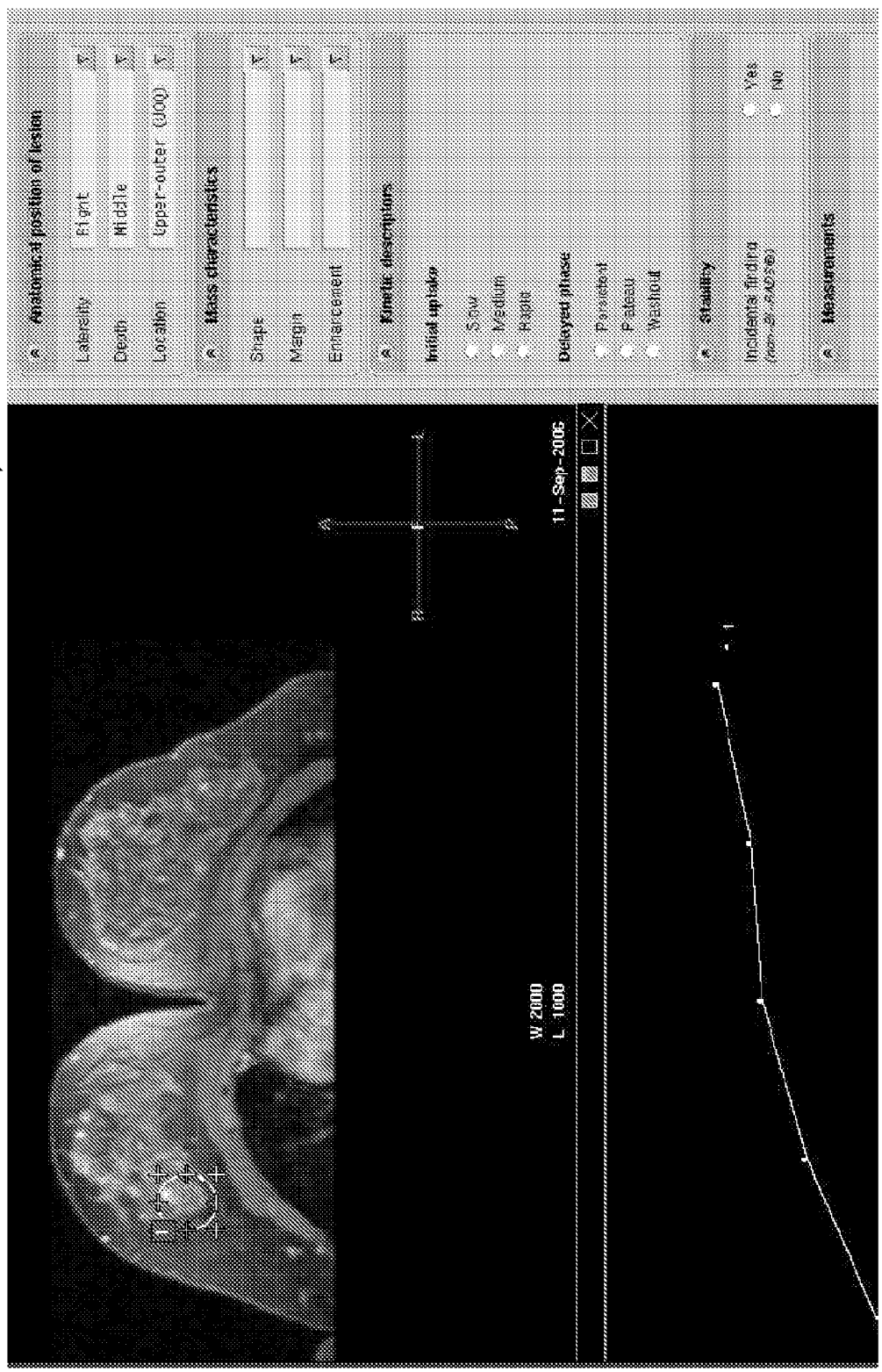
FIG. 1 shows an exemplary screen view of a user-delineated medical image using an annotation tool according to an exemplary embodiment.

The exemplary embodiments may be further understood with reference to the following description of exemplary embodiments and the related appended drawings, wherein like elements are provided with the same reference numerals. The exemplary embodiments are related to systems and methods for intelligently combining medical findings received across different modalities, such as ultrasonic ("US") data, magnetic resonance imaging ("MRI") data, and mammography ("MG") data. As will be described in greater detail below, the exemplary embodiments will allow for physicians (e.g., radiologists, oncologists, etc.) to efficiently compare all current medical images and records of a patient across any modality to any prior medical images and records of that patient. Thus, physicians may be provided with all information available regarding multiple findings from one or more lesions from a patient and easily assess the progression of these lesions.

Solutions have been proposed to help physicians perform such comparison tasks. For instance, the Breast Imaging-Reporting and Data System, or BI-RADS, is a quality assurance tool designed to document breast cancer studies in a structured manner using standardized vocabulary. Specifically, this system allows for radiologists to annotate lesions on images and store the annotations in databases. BI-RADS is a collaborative effort of many health groups, and is published and trademarked by the American College of Radiology ("ARC") in the form of the BI-RADS Atlas. The Atlas is divided into 3 publications, specifically mammography data, ultrasound data, and MRI data. Imaging results are often expressed in terms of the BI-RADS Assessment Category, often called a "BI-RADS score." The categories include: 0=incomplete, 1=normal, 2=benign, 3=indeterminate, 4=suspicious of malignancy, 5=highly suggestive of malignancy, and 6=known biopsy, proven malignancy.

The annotations made on current studies may need to be linked to annotations made in prior studies in order for the physician to easily verify annotation consistency and evaluate any interval developments. As noted above, the current challenge for physicians lies in linking current and prior studies across different modalities. For instance, a patient having breast cancer may have ultrasonic studies, MRI studies, and mammography studies, and it is difficult to link the medical findings across these modalities. Within the exemplary systems and methods of the present disclosure, linking and combining these findings would require the time-consuming and error-prone task of explicitly interpreting and selecting matching findings by the physician. Thus, an exemplary data-linking tool and corresponding method may allow these physicians to easily link these medical findings with limited interference.

Throughout this disclosure, the exemplary embodiments will be directed to the intelligent linking of medical data related to breast cancer and areas of interest, such as lesions. However, it should be noted that the exemplary systems and methods described herein are not limited to breast cancer data, and may be applied to any type of standardized data collection. For instance, the present disclosure may be applied towards collecting, comparing, and reporting data related to various forms of cancer, various types of medical data, various forms of imaging and recording data, etc.

FIG. 1 shows an exemplary screen view 100 of a user-delineated medical image using an annotation tool according to an exemplary embodiment. For instance, the screen view 100 may be a view of a BI-RADS image designed for documenting breast cancer studies in a structured manner using standardized vocabulary. This screen view 100 allows a user to annotate an area of interest, such as a lesion, depicted in the image and store the annotations in a database. As illustrated in the screen view, the annotated data may also include anatomical position of lesion, mass characteristics (e.g., the shape, the margin, enhancement patterns, etc.), kinetic descriptions (e.g., initial uptake, delayed phase, etc.), stability, measurements, as well as many other findings. According to the exemplary embodiments, each of the annotations made by the physician in a current study may be linked to prior annotations made in previous studies. It should be noted that the term "user" may refer to any operator of the systems and methods described herein, including, but not limited, to physicians, radiologists, oncologists, etc.

Figure 2:
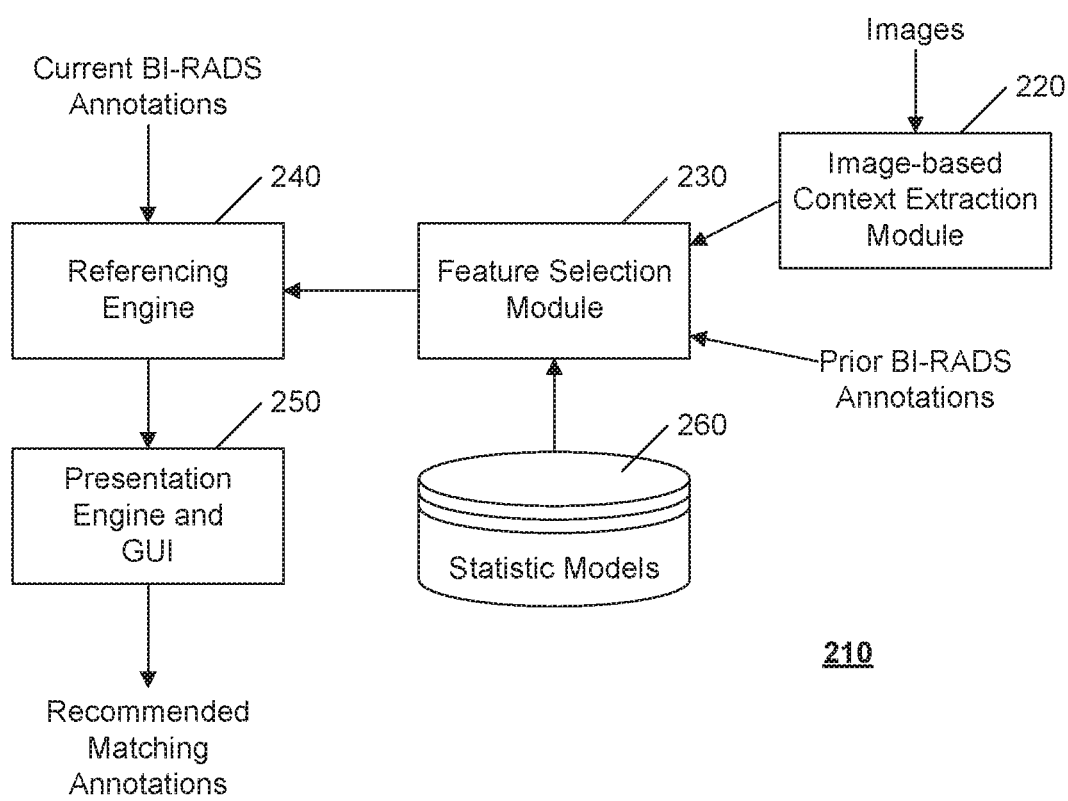
FIG. 2 shows a data-linking tool for intelligently linking medical data received across different modalities according to an exemplary embodiment.

FIG. 2 shows a data-linking tool 210 for intelligently linking medical data received across different modalities according to an exemplary embodiment. The data-linking tool 210, or simply tool, includes various components such as an image-based context extraction module 220, a feature selection module 230, a referencing engine 240, a presentation engine 250, and a database of statistic models 260, some of which can be implemented as software instructions executable by a processor. Furthermore, the exemplary data-linking tool 210 includes a processor and a non-transitory computer readable storage medium, such as a memory. Accordingly, the memory may include the set of software instructions that are executable by the processor. It should be noted that, each of the components 220-250 of the tool 210 may include an individual processor, memory and corresponding instructions, thereby creating a multi-processor architecture for the tool 210.

According to one of the exemplary embodiments, the data-linking tool 210 is a network-based software tool utilizing a communication service to allow physicians to read, create, augment, interpret, compare and correlate medical data in both images and reports.

Typically, physicians create annotations on images of a lesion on a per-modality, per-study basis. The very same lesion can be reviewed numerous times through a combination of ultrasound, MRI, and mammography. For recurring patients, the lesions need to be reviewed using prior image studies as reference points, in addition to any current imaging studies. Thus, a time-saving aspect of the data-linking too 210 would be to allow physicians to have different annotations of the same lesion in various modality to be linked to create a summary of progression made by the lesion.

During a current image study, a physician delineates a lesion on an image such as the image illustrated in screen view 100. The physician then uses an annotation tool, such as the BI-RADS tool, to describe the lesion using standardized terms. For instance, annotations made using the BI-RADS tool may be coded in extensible markup language ("XML") as follows:

```
<?xml version='1.0' encoding='utf-8'?>
<Content>
    <LesionList number="2">
        <Lesion uid="1.3.46.670589.5.2.23.650057008" />
    </LesionList>
    <CurrentFinding>
        <UID>1.3.46.670589.5.2.23.650057008</UID>
        <Modality>MR</Modality>
        <Laterality>Right breast</Laterality>
        <Depth>Medial</Depth>
        <Location>5 o'clock position</Location>
        <Type>Solid mass</Type>
        <Keys number="7">
            <Key Name="Shape" Value="Ovoid shape (Oval)">
            <Key Name="Margin" Value="Spiculated">
            <Key Name="Measurement " Direction="Left-right" Value="1.5mm">
        </Keys>
    </CurrentFinding>
</Content>
```

According to the exemplary embodiments described herein, the image-based context extraction module 220 extracts descriptive medical findings or "contextual information" (e.g., position of a lesion relative to landmarks) of a delineated lesion while the lesion is being annotated by a physician. The contextual information typically describes quantitative aspects of lesions that may not be part of the BI-RADS tool. For example, the location of a lesion is characterized in BI-RADS by laterality, clock-position, and depth. However, the context of the lesion describes the distance of the lesion relative to the nipple, the skin surface, as well as other lesions in the neighborhood. Such contextual information may be needed in order to discern clustered lesions. For instance, the extracted image-based context description of the lesion may be coded in XML as follows:

```
<?xml version='1.0' encoding='utf-8'?>
<Content>
    <LesionList number="2">
    <Lesion uid="1.3.46.670589.5.2.23.650057008" />
    </LesionList>
    <Context>
        <UID>1.3.46.670589.5.2.23.650057008</UID>
        <DistanceToNipple Unit="cm">3</DistanceToNipple>
        <DistanceToSkin Direction="Axial" Unit="cm">1.3</DistanceToSkin>
        <DistancetoLesion uid="1.3.46.670589.5.2.23.650057008" Unit="cm">1</DistancetoLesion>
        <VolumeEstimate Unit="mm3">4</VolumeEstimate>
        <Type Likelihood="0.8">Mass </Shape>
        <Type Likelihood="0.2">Non-Mass-Like Enhancement</Shape>
        <Shape Likelihood="0.7">Oval </Shape>
        <Shape Likelihood="0.3">Round</Shape>
    </Context>
</Content>
```

The feature selection module 230 builds a multi-modal feature vector that includes descriptors of the annotation as well as the extracted contextual information from the annotation. The selection of features is based on statistic models stored in the database 260. Furthermore, the significance, or weight, of each of the selected features may also be retrieved from the database 260.

Using the BI-RADS tool, physicians may annotate the same lesion using different BI-RADS terms. Furthermore, the inter-person agreement varies per descriptor. Statistic models of the database 160 may describe the level of interperson agreement per descriptor. The higher the number is, then the more significance the descriptor has to the referencing engine 240. For example, a model may select "Modality," "Laerality," Depth," "Type," "DistanceToNipple," and "Shape" in order to build a feature vector as follows:

| Features | Annotation values | Context values | Significance |
|---|---|---|---|
| Modality | MR | | 0.05 |
| Depth | Medial | | 0.2 |
| Location | 5 o'clock | | 0.2 |
| Laterality | Right | | 0.5 |
| Type | Mass | Mass = 0.8 No-Mass-Enhancement = 0.2 | 0.2 |
| DistanceToNipple | 3 cm | | 0.1 |
| Shape | Oval | Oval = 0.7 Round = 0.3 | 0.2 |
| ... | | | ... |

The referencing engine 240 links annotations of the same lesion, typically from different modalities or imaging protocols in the same study. In order to determine the likelihood of two annotations referring the same lesion, the referencing engine 240 may use heuristics rules to quantitatively compute a relevance score.

According to the exemplary embodiments described herein, the referencing engine 240 computes a similarity (e.g., a relevance score or significance score) between the exemplary feature vector of the current annotation and a feature vector of a prior annotation or reference annotation. For instance, the similarity between these two vectors may be modeled as a distance (D) between the two vectors. Specifically, D may be defined as a weighted sum of the distances of element features as follows:

$$D = \Sigma m_i * d_i$$

In addition, the distance function $d_i$ may be computed for each feature as follows:

$$d_i = e^{a_i - b_i} * e^{a'_i - b'_i}$$

Wherein $a_i$ and $b_i$ are annotation features, and $a'_i$ and $b'_i$ are the image-based contextual feature corresponding to the annotation features $a_i$ and $b_i$, respectively. When an image feature $a'_i$ has no corresponding annotation feature, it may be assumed that the value of $a_i$ will be empty, and vice versa.

Furthermore, a subtraction operation computes the difference between two arbitrary values of features. For instance, depending on the value of a descriptor (e.g., Modality), it may be a Boolean operation such as:

$$a - b = \begin{cases} 1, & \text{if } a \neq b \\ 0, & \text{otherwise} \end{cases}$$

For descriptors with numerical values, the subtraction operation is defined as a subtraction of values (e.g., DistanceToNipple). For clock-wise locations, the subtraction operation may be defined as follows:

$$a - b = \begin{cases} |a - b|, & \text{if } |a - b| < 6 \\ 12 - |a - b|, & \text{otherwise} \end{cases}$$

For compound descriptor such as context annotations of Mass or Shape, the subtraction operation is defined as the sum of the subtraction of element descriptors. It should be noted that while these exemplary equations may be used to compute a relevance score or significance score between multiple feature vectors, these equations merely provide one example of how these scores may be computed. Accordingly, any number of alternative equations may be used in the comparison of features vectors and the computation and similarity scores.

Finally, the presentation engine 250 of the data-linking tool 210 presents the user with a display of matching annotations based on the similarities computed by the referencing engine 240. According to one exemplary embodiment, the presentation engine 250 interacts with a graphical user interface ("GUI"), wherein the data is displayed to the user and input is received from the user. From this display the user may select a matching annotation from the list, as illustrated in FIG. 3.

Figure 3:
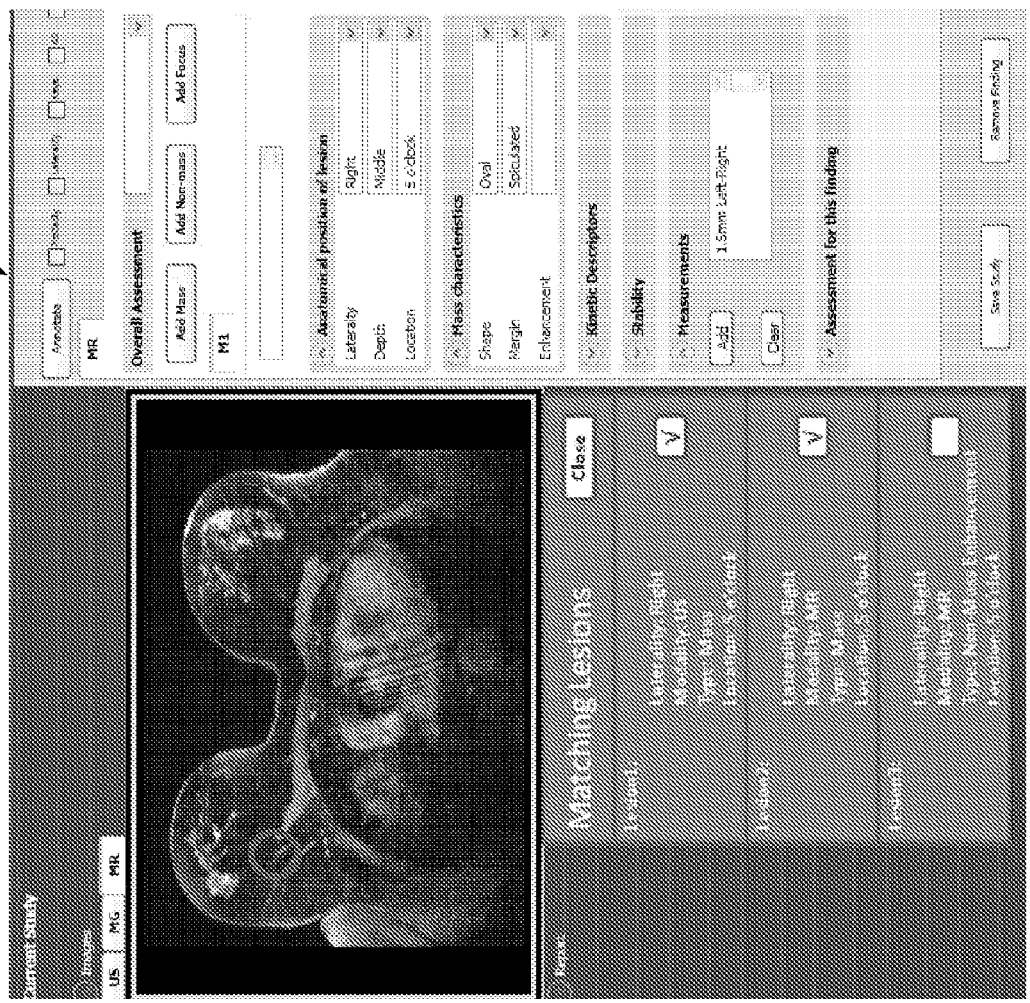
FIG. 3 shows an exemplary screen view of matching annotations received across different modalities according to an exemplary embodiment.

FIG. 3 shows an exemplary screen view 300 of matching annotations received across different modalities according to an exemplary embodiment. As noted above, the display of screen view 300 may be an interactive GUI, wherein the user provides the data-linking tool 210 with input such as an image selection, a request for more detailed information, etc.

The screen view 300 includes a "Images" section, wherein the user may select an image from different modalities, such as an ultrasound image, a mammography image, and an MRI image. The screen view 300 also includes a "Report" section, wherein the user may select different lesions from a list of matching lesions. The screen view 300 further includes an "Annotate" section, wherein the user may input various detailed annotations for a selected image. These detailed annotations may include adding a new mass, adding a non-mass, add a focus region, etc. Additional detailed annotations may include, but are not limited to, anatomical position of lesion, mass characteristics (e.g., the shape, the margin, enhancement patterns, etc.), kinetic descriptions (e.g., initial uptake, delayed phase, etc.), stability, measurements, etc.

In addition to these annotations, the screen view 300 includes an "Assessment" section, wherein the user may input an assessment, as well as medical notes related to this specific finding. Whenever the user provides or adjust input within the GUI of the screen view 300, the user may save the study to the database 260 of the tool 210. Alternatively, the user may also remove the finding or delete the study from the database 260 once it is no longer needed.

Figure 4:
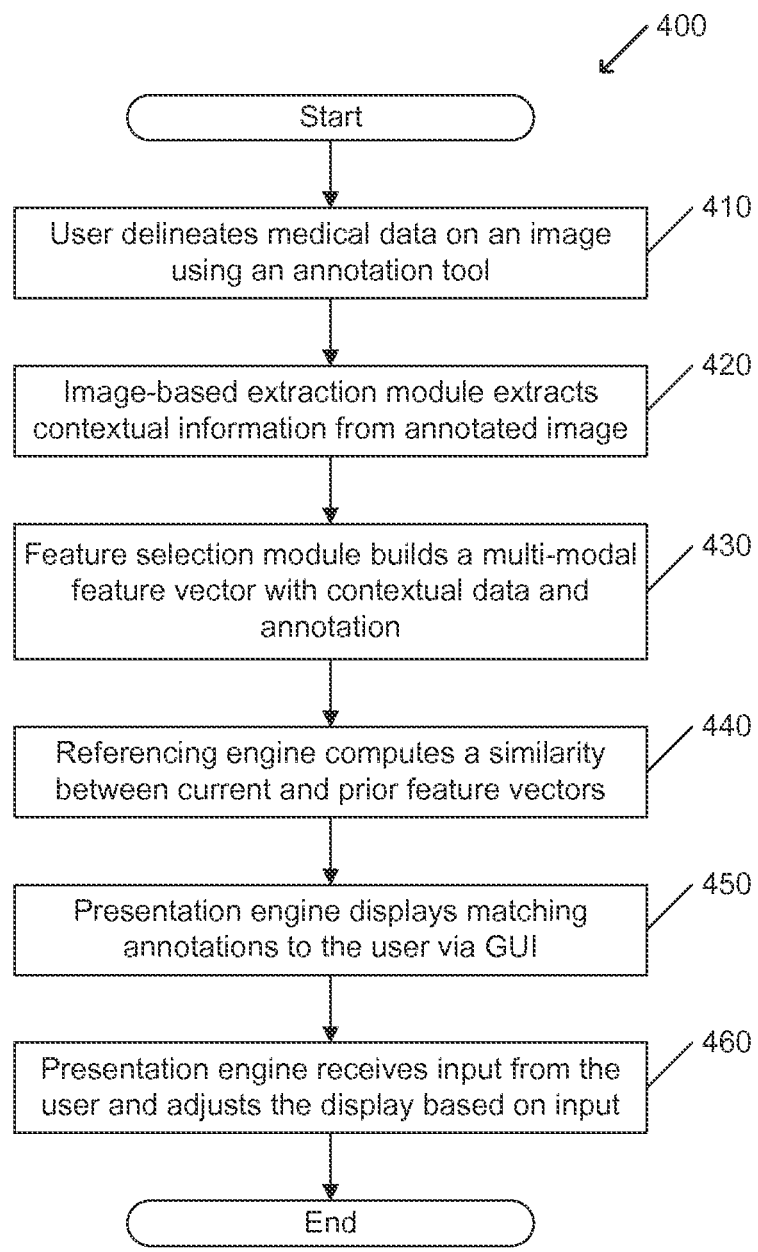
FIG. 4 shows an exemplary method for intelligently linking medical data received across different modalities according to an exemplary embodiment.

FIG. 4 shows an exemplary method 400 for automating workflow of assigning work orders and tracking the process according to an exemplary embodiment. It should be noted that method 400 that will be discussed with reference to data-linking tool 210 and components of the system 200 of FIG. 2. As detailed above, the data-linking tool 210 allows for users to combine different modalities of the same lesion in order for a summary of the progression may be effectively and efficiently obtained by the user.

Beginning with step 410, the data-linking tool 210 receives medical data from a user. As noted above, the user may delineate medical data, such as lesions, on an image using an annotation tool. For instance, the user may provide annotations to a current image using a standardized annotation tool such as the BI-RADS tool. The BI-RADS annotations may be coded in XML and transmitted to the referencing engine 240 for processing.

In step 420, the image-based extraction module 220 of the tool 210 extracts contextual information from the annotated image provided by the user. As noted above, the contextual data may include information otherwise not available via the annotation tool. This contextual information may include descriptive data, relative distance to a landmark (e.g., nipple, skin surface, etc.), pathological findings (e.g., another lesion in the vicinity), etc. Similar to the BI-RADS annotations, the contextual data may be coded in XML and transmitted to the referencing engine 240 for processing.

In step 430, the feature-selection module 230 of the tool 210 builds a multi-modal feature vector using the extracted contextual data and the annotations from the user. As noted above, the selection of features may be based on statistic models stored in the database 260 and a weight factor (e.g., a relevance score) of the selected features may be retrieved and built into the multi-modal feature vector.

In step 440, the referencing module 240 computes a similarity between the feature vector of the current annotation and a reference feature vector of a prior annotation. Specifically, the referencing module 240 computes a weighted sum of all the distances between each of the elements of the two vectors. In other words, a relevance score is computed for each of the annotation features from the current feature vector in relation to a prior feature vector (e.g., a reference vector). Accordingly, the referencing module 240 sorts relevant annotations and provide a list of the most relevant annotation scores to the presentation module 250.

In step 450, the presentation module 250 displays any matching annotations between the feature vector and the reference feature vector to the user via the GUI. The exemplary GUI may be a web-based portal accessible to one or more physicians on a network.

In step 460, the data-linking tool 210 receives further input from the user such as a selection of an image, a request for more detailed information, etc. Accordingly, the presentation module 250 adjusts the display on the GUI based on the received further input from the user.

Once annotations are linked through the data-linking tool 210, a summary of the progression (e.g., changes in volume, shape, margin, etc.) for each lesion may be generated. Accordingly, this summary may be applied to any number of breast cancer studies and reporting services, such as, for example the "Cancer Care Companion" and "Integral Breast" of Clinical Information Solutions and "MammoTrack" products from Koninklijke Philips Electronics N.V of Eindhoven, The Netherlands.

Those skilled in the art will understand that the above-described exemplary embodiments may be implemented in any number of manners, including, as a separate software module, as a combination of hardware and software, etc. For example, the data-linking tool 210 may be a program containing lines of code stored on a non-transitory computer readable storage medium that, when compiled, may be executed on a processor.

It is noted that the claims may include reference signs/numerals in accordance with PCT Rule 6.2(b). However, the present claims should not be considered to be limited to the exemplary embodiments corresponding to the reference signs/numerals.

It will be apparent to those skilled in the art that various modifications may be made in the present invention, without departing from the spirit or the scope of the invention. Thus, it is intended that the present invention cover modifications and variations of this invention provided they come within the scope of the appended claimed and their equivalents.

What is claimed is:

1. A system, comprising:
    an extraction module extracting contextual information from an image of an area of interest of a patient including annotations;
    a feature selection module building a current feature vector using the extracted contextual information and the annotations;
    a referencing engine computing a similarity score between the current feature vector and a prior feature vector of a prior image of the patient; and
    a presentation engine providing a display based on the similarity score,
    wherein the similarity score (D) is computed as a weighted ($m_i$) sum of distances ($d_i$) between each element of the current feature vector and the prior feature vector, wherein:

$$D = \Sigma m_i * d_i; \text{ and}$$

wherein distances ($d_i$) of annotation features ($a_i$) and ($b_i$), and contextual features ($a'_i$) and ($b'_i$) are computed as:

$$d_i = e^{a_i - b_i} * e^{a'_i - b'_i}.$$

2. The system of claim 1, wherein the presentation engine displays matching annotations between the image and the prior image.

3. The system of claim 1, wherein the presentation engine receives input from a user via a user interface and adjusts the image based on the input.

4. The system of claim 3, wherein the input received from the user includes at least one of an image selection, an adjusted detail, an assessment, and a request for additional information.

5. The system of claim 1, wherein the annotations include at least one of an image modality reading, a laterality reading, a depth reading, a location reading, a type reading, a shape reading, and a measurement reading.

6. The system of claim 1, wherein the contextual data includes at least one of a relative distance to nipple, a relative distance to skin surface, a relative distance to lesion, a volume estimate, a type likelihood, and a shape likelihood.

7. The system of claim 1, wherein the area of interest is a lesion from a breast cancer patient.

8. The system of claim 1, wherein the image and the prior image are of the same area of interest using different imaging protocols, and wherein the imaging protocols includes at least one of ultrasonic imaging, magnetic resonance imaging ("MRI") imaging, and mammography ("MG") imaging.

9. A method, comprising:
    extracting, by an extraction module, contextual information from an image of an area of interest of a patient including annotations;
    building, a feature selection module, a current feature vector using the extracted contextual information and the annotations;
    computing, by a referencing engine, a similarity score between the current feature vector and a prior feature vector of a prior image of the patient, wherein the similarity score (D) is computed as a weighted ($m_i$) sum of distances ($d_i$) between each element of the current feature vector and the prior feature vector; and
    displaying, by a presentation engine, a presentation based on the similarity score, wherein:

$$D = \Sigma m_i * d_i; \text{ and}$$

wherein distances ($d_i$) of annotation features ($a_i$) and ($b_i$), and contextual features ($a'_i$) and ($b'_i$) are computed as:

$$d_i = e^{a_i - b_i} * e^{a'_i - b'_i}.$$

10. The method of claim 9, further comprising:
    displaying, by a presentation engine, matching annotations between the image and the prior image.

11. The method of claim 9, further comprising:
    receiving input from a user via a user interface; and
    adjusting the image based on the input.

12. The method of claim 11, wherein the input received from the user includes at least one of an image selection, an adjusted detail, an assessment, and a request for additional information.

13. The method of claim 9, wherein the annotations include at least one of an image modality reading, a laterality reading, a depth reading, a location reading, a type reading, a shape reading, and a measurement reading.

14. The method of claim 9, wherein the contextual data includes at least one of a relative distance to nipple, a relative distance to skin surface, a relative distance to lesion, a volume estimate, a type likelihood, and a shape likelihood.

15. The method of claim 9, wherein the area of interest is a lesion from a breast cancer patient.

16. The method of claim 9, wherein the image and the prior image are of the same area of interest using different imaging protocols, and wherein the imaging protocols includes at least one of ultrasonic imaging, magnetic resonance imaging ("MRI") imaging, and mammography ("MG") imaging.

17. A non-transitory computer readable storage medium including a set of instructions that are executable by a processor, the set of instructions being operable at least to:
   extract contextual information from an image of an area of interest of a patient including annotations;
   build a current feature vector using the extracted contextual information and the annotations; and
   compute a similarity score between the current feature vector and a prior feature vector of a prior image of the patient, wherein the similarity score (D) is computed as a weighted ($m_i$) sum of distances ($d_i$) between each element of the current feature vector and the prior feature vector;
   provide a display presentation based on the similarity score (D), wherein:

$D = \Sigma m_i * d_i$; and wherein distances ($d_i$) of annotation features ($a_i$) and ($b_i$), and contextual features ($a'_i$) and ($b'_i$) are computed as:

$d_i = e^{a_i - b_i} * e^{a'_i - b'_i}$.

18. The non-transitory computer readable storage medium of claim 17, wherein the set of instructions are further operable to:
   display matching annotations between the image and the prior image;
   receive input from a user via a user interface; and
   adjust the image based on the input.

19. The non-transitory computer readable storage medium of claim 17, wherein the annotations include at least one of an image modality reading, a laterality reading, a depth reading, a location reading, a type reading, a shape reading, and a measurement reading.

20. The non-transitory computer readable storage medium of claim 17, wherein the image and the prior image are of the same area of interest using different imaging protocols, and wherein the imaging protocols includes at least one of ultrasonic imaging, magnetic resonance imaging ("MRI") imaging, and mammography ("MG") imaging.

* * * * *